United States Patent [19]

Blacker et al.

[11] Patent Number: 5,637,738

[45] Date of Patent: Jun. 10, 1997

[54] PROCESSES FOR PREPARING 1,2-EPOXY-1,2,3,4-TETRAHYDRONAPHTHALENES

[75] Inventors: Andrew J. Blacker, North Rigton; Stephen M. Brown, Upper Cumberworth; Derek R. Boyd, Maryville Park; Gary N. Sheldrake, Kirkburton, all of United Kingdom

[73] Assignee: Zeneca Limited, London, England

[21] Appl. No.: 507,470

[22] PCT Filed: Feb. 26, 1994

[86] PCT No.: PCT/GB94/00307

§ 371 Date: Aug. 25, 1995

§ 102(e) Date: Aug. 25, 1995

[87] PCT Pub. No.: WO94/19338

PCT Pub. Date: Sep. 1, 1994

[30] Foreign Application Priority Data

Feb. 26, 1993 [GB] United Kingdom .................. 9320468

[51] Int. Cl.$^6$ .................................................. C07D 301/02
[52] U.S. Cl. .................... 549/518; 549/433; 549/545; 558/44; 558/46; 558/270; 558/276; 558/482
[58] Field of Search ............................................. 549/518

[56] References Cited

U.S. PATENT DOCUMENTS 4,082,773  4/1978  Hauck ....................... 549/433

FOREIGN PATENT DOCUMENTS 329563   8/1989   European Pat. Off. .
2603589  8/1977   Germany .

OTHER PUBLICATIONS

Becker et al., J. Am. Chem. Soc. (1979), 101 (19) pp. 5679–5687.

White, et al: "Photolysis of cis–1, 2–dihydroxyindancarbonate and cis–1, 2–dihydroxy–1,2,3,4–tetrahydronaphthalene carbonate", Chemical Abstracts, vol. 110, No. 25, issued 1989, Jun. 19, p. 631, col. 2, No. 231 476r; & J. Heterocycl. Chem. 1988, 25(6), 1781–3.

*Primary Examiner*—Johann Richter
*Assistant Examiner*—Laura L. Stockton
*Attorney, Agent, or Firm*—Cushman Darby & Cushman IP Group Pillsbury Madison & Sutro LLP

[57] ABSTRACT

Described herein is a process for the preparation of (1S,2R)-1,2-epoxy-1,2,3,4-tetrahydronaphthalene having the Formula (I):

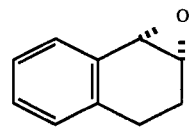

Formula (I)

which comprises the steps of
(a) hydrogenating the compound of Formula (II) to form cis-(1R, 2S)-1,2-dihydroxy-1,2,3,4-tetrahydronaphthalene having the Formula (V):

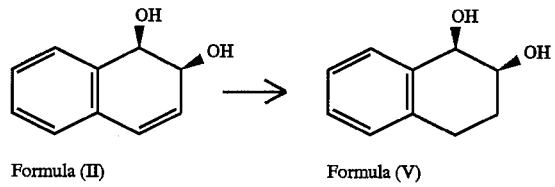

Formula (II)           Formula (V)

(b) reacting the dihydroxy compound of Formula (V) with a sulphonyl halide of formula $R^1SO_2Z$ wherein $R^1$ is methyl, ethyl, trifluoromethyl, phenyl or p-tolyl, and Z is fluorine, chlorine, bromine or iodine to give a bis-sulphonyl ester of formula (X):

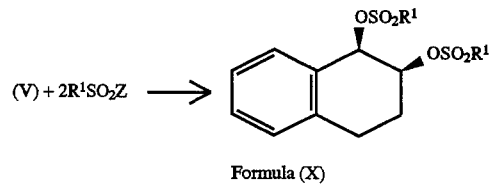

Formula (X)

and (c) treating the bis-sulphonyl ester (X) with an alkali metal carbonate or alkali metal hydroxide to give the compound of Formula (I).

2 Claims, No Drawings

PROCESSES FOR PREPARING 1,2-EPOXY-1,2,3,4-TETRAHYDRONAPHTHALENES

This application is a 371 of PCT GB94/00307 filed Feb. 26, 1994.

This invention relates to chemical processes, and in particular to processes for making (1S,2R)-1,2-epoxy-1,2,3,4-tetrahydronaphthalene having the Formula (I):

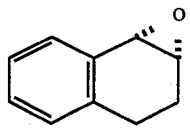

Formula (I)

and the enantiomer thereof having the Formula (IA):

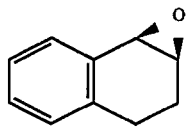

Formula (IA)

Compounds of Formulae (I) and (IA) are useful as intermediates for the synthesis of biologically active compounds, for example pharmaceutical compounds. As epoxides they are capable of undergoing a variety of reactions enabling preparation of a wide range of further products.

According to the present invention there is provided a process for the preparation of (1S,2R)-1,2-epoxy-1,2,3,4-tetrahydronaphthalene having the Formula (I) which comprises the steps of
(a) hydrogenating the compound of Formula (II) to form cis-(1R,2S)-1,2-dihydroxy-1,2,3,4-tetrahydronaphthalene having the Formula (V):

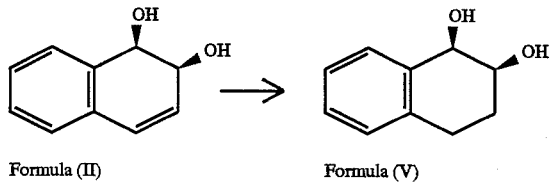

Formula (II)  Formula (V)

(b) reacting the dihydroxy compound of Formula (V) with a sulphonyl halide of formula $R^1SO_2Z$ wherein $R^1$ is methyl, ethyl, trifluoromethyl, phenyl or p-tolyl, and Z is fluorine, chlorine, bromine or iodine to give a bis-sulphonyl ester of Formula (X):

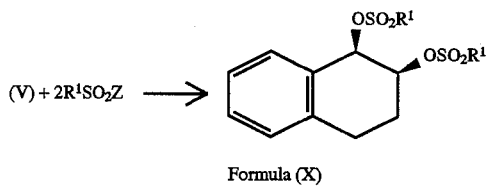

Formula (X)

and (c) treating the bis-sulphonyl ester (X) with an alkali metal carbonate or alkali metal hydroxide to give the compound of Formula (I).

The hydrogenation Step (a) of the present process may be carried out by standard procedures for example by reacting a solution of compound (II) with hydrogen in the presence of a metal catalyst. The metal catalyst may be any hydrogenation catalyst such as those comprising Raney nickel, platinum, palladium, ruthenium or rhodium which may be used as a finely divided free metal or metal oxide or as a metal or metal oxide carried on a support selected from charcoal, alumina or silica. The metal catalyst is preferably supported on charcoal, more preferably is from 0.5 to 10% platinum or palladium on charcoal and especially 10% palladium on charcoal. Conveniently the compound (II) may be dissolved or dispersed in a liquid medium such as a lower alcohol, preferably methanol or ethanol for the hydrogenation reaction. The reaction may be performed at a temperature from 0° C. to 100° C. and is preferably performed at temperatures from 20° C. to 25° C. The product (V) may be recovered by filtering off the catalyst and evaporating the filtrate. The product may be purified by conventional methods such as recrystallisation.

In step (b) the sulphonyl halide is preferably reacted with the dihydroxy compound (V) in the presence of a tertiary amine as an acid acceptor. Examples of tertiary amines include triethylamine, pyridine and dimethylaniline. The reaction is preferably conducted in an inert solvent at a temperature from −30° C. to 10° C. preferably at from −20° C. to 5° C. and especially at from 0° to 5° C. Examples of suitable solvents include ethers such as diethylether or tetrahydrofuran, hydrocarbons such as benzene, toluene or xylene and halogenated hydrocarbons such as dichloromethane, chloroform and dichloroethane. At the end of the reaction the tertiary amine hydrohalide formed may be removed by filtration and the bis-sulphonyl ester may be recovered by evaporation of the filtrate, and further purified by conventional means such as recrystallisation. Preferred sulphonyl halides are selected from methane-, trifluoromethane- and p-toluenesulphonyl chlorides.

In stage (c), the alkali metal carbonate may be, for example sodium or potassium carbonate. The alkali metal hydroxide may be sodium or potassium hydroxide. The reaction may be performed in water or a mixture of water and a lower alcohol preferably methanol or ethanol and may be carried out at a temperature of from −70° C. to 100° C. preferably from −20° C. to 70° C. and more preferably from 0° C. to 40° C. Alternatively stage (c) may be carried out in a mixture of water and immiscible organic solvent preferably a halogenated alkane such as dichloromethane, chloroform or carbon tetrachloride, a hydrocarbon such as benzene, toluene or xylene, an ether such as diethylether, tertiary butyl methylether or tetrahydrofuran. A phase transfer catalyst, such as a tetraalkylammonium halide preferably tetrabutylammonium bromide may optionally be added to the reaction mixture. The reaction is preferably well stirred to achieve good mixing of solvents and efficient action of the phase transfer catalyst. The epoxide (I) may be isolated from the reaction mixture by standard procedures such as solvent extraction followed by evaporation of the solvent.

According to a further feature of the present invention there is provided a process for the preparation of (1R,2S)-1,2-epoxy-1,2,3,4-tetrahydronaphthalene having the Formula (IA) which comprises the steps of a) hydrogenating the compound of Formula (II) to form cis-(1R,2S)-1,2-dihydroxy-1,2,3,4-tetrahydronaphthalene of Formula (V):

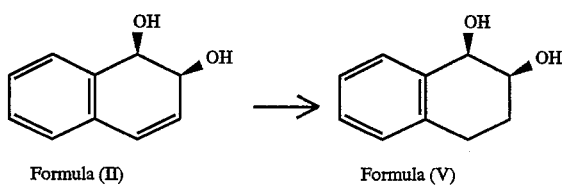

Formula (II) → Formula (V)

b) reacting the compound of Formula (V) with an alkyl orthoalkanoate ester of Formula (VI) to form a mixture of dioxolane diastereoisomers of Formula (VII) and Formula (VIIB):

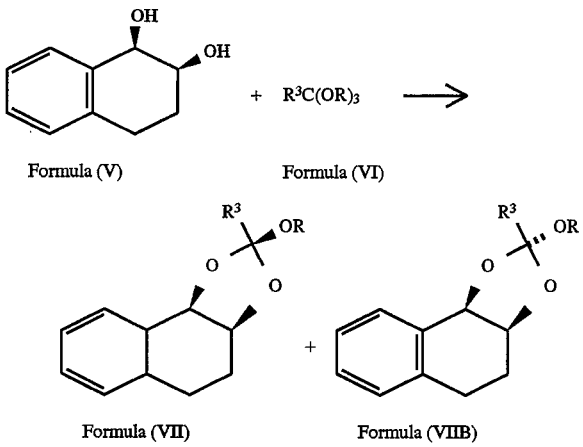

Formula (V)   Formula (VI)

Formula (VII)   Formula (VIIB)

in which R is alkyl and $R^3$ is H, alkyl or phenyl;

c) reacting the mixture of dioxolane diastereoisomers of Formulae (VII) and (VIIB) with a halotrialkyl- or halotriarylsilane of Formula (XIV) to form a compound of Formula (IX):

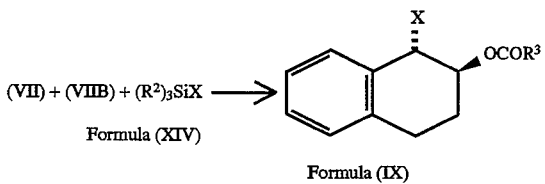

(VII) + (VIIB) + $(R^2)_3SiX$ →

Formula (XIV)

Formula (IX)

in which:
$R^2$ is alkyl or aryl;
X is —Cl, —Br or —I; and
$R^3$ is as hereinbefore defined.

d) reacting the compound of Formula (IX) with an alkali metal alkoxide to form (1R,2S)-1,2-epoxy-1,2,3,4-tetrahydronaphthalene having the Formula (IA).

In step (a) of the above process, the hydrogenation may be carried out as described for hydrogenation of compound (II) above. In step (b) the reaction of the alkyl orthoalkanoate ester (VI) with the dihydroxy compound (V) may be carried out by heating the reactants in an inert medium, preferably in a hydrocarbon solvent such as benzene, toluene, or xylene in the presence of a catalytic amount of an acid, preferably an organic acid such as benzoic acid or p-toluenesulphonic acid. The reaction is preferably carried out at a temperature of from 60° C. to 120° C. The alkyl group R in compounds (VII), (VIIB) and (IX) is preferably methyl or ethyl. The group $R^3$ is preferably H, $C_{1-6}$-alkyl or phenyl. In step (c) the dioxolanes (VII) and (VIIB) may be treated with a halotrialkylsilane or a halotriarylsilane such as chloro-, bromo- or iodotrimethylsilane to give the corresponding halo-compound (IX, X=Cl, Br or I). Chlorotriphenylmethane or bromotriphenylmethane may be used instead of chlorotrimethylsilane to prepare (IX, X=Cl, Br). Where $R^2$ is alkyl it is preferably $C_{1-6}$-alkyl, more preferably methyl and where $R^2$ is aryl it is preferably phenyl. X is preferably chloro. In step (d) the alkali metal alkoxide is preferably an alkali metal $C_{1-4}$-alkoxide more preferably sodium or potassium methoxide, ethoxide or butoxide and especially sodium methoxide. Reaction of the compound of Formula (IX) with the alkali metal alkoxide may be performed in a liquid medium preferably in an ether such as tetrahydrofuran. The compound (IA) may be isolated by evaporating the liquid medium and may be purified by crystallisation.

The halo substituent of compound (IX) may be reacted with nucleophilic reagents to give further 1,2-substituted-1,2,3,4-tetrahydronaphthalenes.

The compounds of the present invention may be used to prepare other useful intermediates. For example:

(i) reacting cis-(1R,2S)-1,2-dihydroxy-1,2,-dihydronaphthalene (II) with an epoxidising agent forms cis-(1R,2S)-1,2-dihydroxy-syn-3,4-epoxy-1,2,3,4-tetrahydronaphthalene (III):

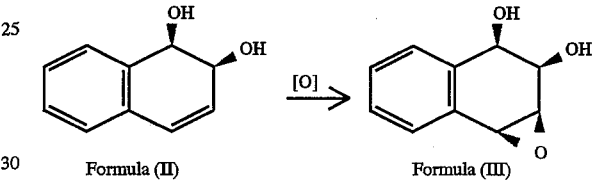

Formula (II)   Formula (III)

(ii) reacting the epoxide (III) with a dehydroxylating agent forms (1S,2R)-1,2-epoxy-1,2-dihydronaphthalene (IV):

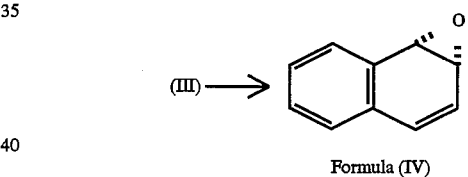

(III) →

Formula (IV)

and (iii) hydrogenating the compound of Formula (IV) forms the compound of Formula (I).

The compound of Formula (III) is novel and forms a further part of the present invention.

In (i) above, the epoxidising agent is not critical, and any of a number of epoxidising agents may be used. The epoxidising agent may be, for example, a per acid such as m-chloroperbenzoic acid. The epoxidation reaction may be carried out under conditions usual for such reactions. Thus for example, the dihydronaphthalene (II) is conveniently dissolved in a chlorinated hydrocarbon solvent, for example dichloromethane or chloroform, and is treated with for example m-chloroperbenzoic acid, preferably in an excess of the amount theoretically required. The reaction is preferably performed at below ambient temperature, for example at 0°–5° C. Preferably the reaction is performed in the presence of an aqueous buffer solution having a pH of 8. The product may be recovered from the reaction mixture by standard methods, for example by separating the aqueous and organic solutions, and recovering the product by evaporating the organic solution. It is surprising that the syn-epoxide is formed; the anti-epoxide would have been expected.

In (ii) above the dehydroxylating agent may be, for example, a combination of chlorotrimethylsilane (two molar proportions) and sodium iodide, used in a solvent (e.g. acetonitrile) at ambient temperature from 20° C. to 25° C. Other suitable dehydroxylation procedures include treatment with triethylorthoformate at 110° C. followed by acetic acid, or treatment with a mixture of dimethyl formamide and acetic acid at 100° C.

Hydrogenation of the epoxide (IV) may be carried out as previously described to give compound (V).

In addition to its use for preparing the epoxide (I), the bis-sulphonyl ester (X) may be used to prepare other useful intermediates. By reaction with sodium nitrate, it may be converted to the bis-nitro ester (XI):

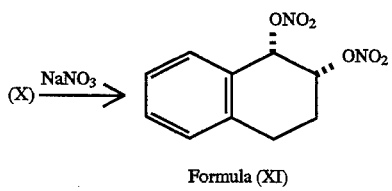

Formula (XI)

The bis-nitro ester (XI) may in turn be hydrogenated in presence of a catalyst to provide the diol (XII):

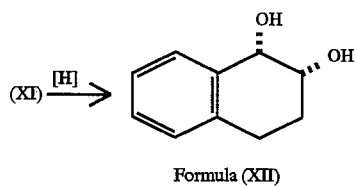

Formula (XII)

Alternatively, to obtain the diol (XII), the bis-sulphonyl ester (X) may be reacted with an alkali metal acetate, for example caesium acetate, to give the bis-acetyl ester (XIII):

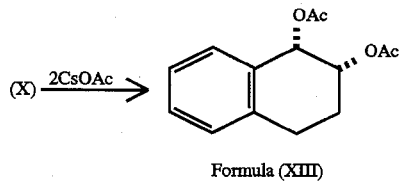

Formula (XIII)

The bis-acetyl ester (XIII) may then be hydrolysed under acidic conditions to give the diol (XII).

Certain of the compounds disclosed above are new and these form a further aspect of the present invention. These include the following compounds:

Compound (III) and its enantiomer of structure (IIIA):

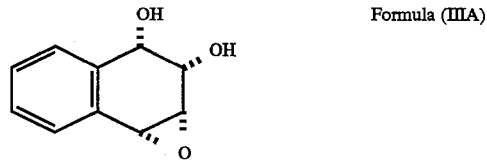

Formula (IIIA)

Compounds of Formula (VII) and (VIIB) wherein R is alkyl preferably methyl or ethyl and $R^3$ is preferably H, $C_{1-6}$-alkyl or phenyl, and their enantiomers of structure (VIIA) and (VIIC):

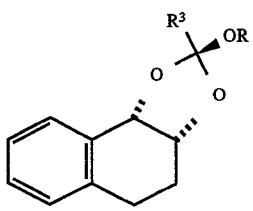

Formula (VIIA)

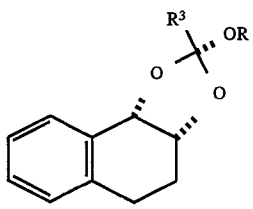

Formula (VIIC)

Compounds of Formula (IX) and their enantiomers of structure (IXA):

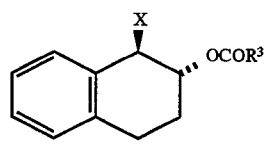

Formula (IXA)

wherein X is —Cl, —Br or —I and $R^3$ is H, alkyl or phenyl.

Compounds of Formula (X) and their enantiomers of Formula (XA):

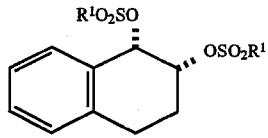

Formula (XA)

wherein $R^1$ is as hereinbefore defined.

The compound of Formula (XI) and its enantiomer (XIA):

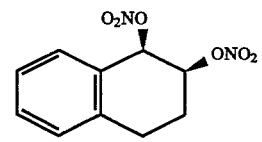

Formula (XIA)

Where the preparation of particular compounds herein has not been specifically described, such compounds may be prepared by application of the processes described above or obvious extension thereof, or by conventional processes known to those skilled in the art, utilising as starting materials appropriate compounds as those described in this specification.

The compound of Formula (II) (cis-(1R,2S)-dihydroxy-1,2-dihydronaphthalene) is a known compound and may be prepared, for example, from naphthalene, using a biochemical process in which naphthalene is introduced into a culture of a mutant strain of the microorganism *Pseudomonas putida*, as described in Example 8 of European Patent 0076606 B1. As set forth in Example 8, the naphthalene may be added to the culture as a solid. It may also be introduced into the culture as a solution in an inert organic apolar solvent. Examples of such solvents include alkanes, which may be straight-chain, branched or cyclic alkanes, preferably having from 8 to 20 carbon atoms. Preferred alkanes include decane, dodecane and hexadecane, or mixtures thereof. Other examples of such solvents include haloalkanes, for example carbon tetrachloride, dichloroethane, trichloroethane and tetrachloroethane; petroleum ethers which are free of aromatic hydrocarbons, preferably the higher-boiling fractions; and alkyl esters of alkanoic acids wherein the alkyl group has more than two carbon atoms and the alkanoic acid more than four. Preferably the alkyl group and the alkanoic acid each have more than 8 carbon atoms, and the sum of their carbon atoms is preferably more than 10. Examples of such solvents include ethyl butanoate, hexyl hexanoate and octyl octanoate.

The cells of the *P. putida* strain may be used as a cell suspension, or they may be immobilised. Immobilisation may be achieved by entrapping the cells in an inert support such as chitosan, a carrageenan alginate salt, a carrageenan polysaccharide, a synthetic polymer such as polyacrylamide, or cellulose acetate. Alternatively, the cells may be aggregated covalently or passively, or adsorbed. Preferably the cells are entrapped on an inert support. Immobilising the cells has the advantage that the amount of cellular debris is reduced; such debris causes difficulties in the isolation of the dihydroxy compound of Formula (II). Immobilisation also makes the separation of the cells from the culture medium easier at the end of the reaction, since it enables their separation by filtration rather than centrifugation. Furthermore, the life of the active cells may be extended.

The enantiomer of compound (II) of structure (IIA) below:

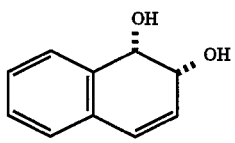

Formula (IIA)

may be prepared from racemic-1,2-dihydro-1,2-dihydroxy naphthalene using a biochemical process as detailed in present Example 4. The racemic-1,2-dihydro-1,2-dihydroxynaphthalene may be prepared by reducing 2,3-epoxy-2,3-dihydro-1,4-naphthoquinone with $NaBH_4$ in ethanol to give 1,4-dihydroxy-2,3-epoxy-1,2,3,4-tetrahydronaphthalene which is reacted with a mixture of sodium iodide, sodium acetate, zinc dust and acetic acid to give 1,2-dihydroxy-1,2-dihydronaphthalene. Compound Formula (IIA) may be reacted with an epoxidising agent as described above to form the compound of Formula (IIIA). The compound of Formula (IIA) may be reacted with an alkylorthoalkanoate as described above to form the compound of Formula (IIIA). The compound of Formula (IIIA) may be reacted with a halotrialkylsilane or a halotriarylsilane as described above to form the compound of Formula (IXA). The compound of Formula (IIA) may be hydrogenated as described above to form a compound of Formula (VA):

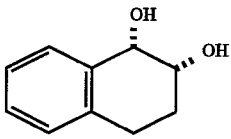

Formula (VA)

The compound of Formula (VA) may be reacted with a sulphonyl halide as described above to form a compound of Formula (XA). The compound of Formula (XA) may be reacted with sodium carbonate as described above to form a compound of Formula (IA). The compound of Formula (XA) may be reacted with sodium nitrate as described above to form a compound of Formula (XIA).

The invention is illustrated further by the following Examples:

EXAMPLE 1

Preparation of (1S,2R)-1,2-epoxy-1,2,3,4-tetrahydronaphthalene (I)

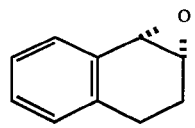

i) Preparation of cis-(1R,2S)-1,2-dihydroxy-1,2-dihydronaphthalene (II).

a) Inoculum Preparation

The inoculum was prepared by picking off several active colonies of *Pseudomonas putida* UV-4 growing on agar plates with 0.1% (w:v) pyruvate. The colonies were transferred using sterile techniques to 10 ml of 0.85% saline solution in a 25 ml sterile jar. The cells were uniformly dispersed in the solution by vigorously vortexing for several minutes. This solution was transferred, again using sterile techniques to a 1 liter baffled side arm inoculum flask, and plugged with a foam bung. The flask contained 200 ml of Seed 2 medium (Seed 2 consists of potassium phosphate, sodium phosphate, ammonium sulphate, magnesium sulphate, ferric chloride at pH 7.2) and 0.6% pyruvate.

Flasks so prepared were shaken at 300 rpm on an orbital shaker at 28° C. overnight, during which the cells grew to an approximate dry cell weight of 3 g/l. The activity of the cells was measured using the standard activity assay and if >14 units/hour the inoculum was used to inoculate the fermenter. Several flasks were prepared in parallel to enable an inoculum of high activity to be selected.

b) Fermentation

A 30 liter fermenter containing 25 liters of Seed 2 medium and 5 g/l glucose at pH 7.0 was inoculated with 200 ml of inoculum prepared as above. The fermenter was sparged with air and vigorously stirred to maintain a high level of dissolved oxygen. The pH of the broth is maintained at 7.0, and antifoam (polyethylene glycol or a polysiloxane) was added as necessary to prevent foaming over. The temperature of the formenter was held at 28° C. When the initial concentration of glucose dropped to 0.5 g/l a glucose feed pump was switched on to deliver glucose at 1 gram per liter per hour for 4 hours. The feed rate was increased to 3 g/l/hour after 4 to 6 hours, maintaining the culture in carbon limitation. The fermentation was continued until the desired dry cell weight and required activity of the cells was reached—generally 20 g/l dry cell weight and an activity of >14 units/hour.

The cells were harvested by centrifugation in 1 liter bottles. The cell pellets can be stored at 3° C. for several days without significant loss of activity.

c) Biotransformation

A 5 liter bio-reactor containing 4.5 liters of potassium phosphate buffer pH 7.6 and 3 g/l ethanol was inoculated with active cells to give 3 g/l dry cell weight. The solution was sparged with air and vigorously stirred to maintain a high concentration of dissolved oxygen. The temperature was maintained at 28° C. and the pH at 7.6 by addition of KOH as necessary. Naphthalene was introduced as a solid at a rate of 12 g/hour. The reaction was monitored by following the change in absorbance at 261 nm—corresponding to λmax of the dihydroxydihydronaphthalene. After 8 hours the reaction was terminated by stopping the stirrer and air supply and removing the cells from the liquor by centrifugation. The cell free liquor was stored at 3° C. and pH 8.5.

d) Isolation of Product

Cis-(1R,2S)-1,2-dihydroxy-1,2-dihydronaphthalene was extracted from the aqueous liquor by stirring with an equal volume of dichloromethane. The dichloromethane layer was separated and the aqueous solution was extracted with a further volume of dichloromethane. The above process was repeated a total of 3 times. The dichloromethane fractions were combined, dried over $Na_2SO_4$, filtered and most of the solvent removed by vacuum distillation. The crude concentrated product formed was poured into n-hexane to precipitate a purer product. Most of the impurities were separated from the product in this way. Further purification was carried out by recrystallisation from 1,2-dichloroethane. 100 g of naphthalene were introduced into the reactor and 36 g of clean cis-(1R,2S)-1,2,-dihydroxy-1,2-dihydronaphthalene were obtained.

ii) Preparation of cis-(1R,2S)-1,2-dihydroxy-1,2,3,4-tetrahydronaphthalene (V).

To a solution of 1 equivalent of cis-(1R,2S)-1,2-dihydroxy-1,2-dihydronaphthalene (II) ($[\alpha]_D^{23}$=+243°, C=0.175, $CHCl_3$) in 10 equivalents of methanol, 0.05 equivalents of 10% palladium on carbon catalyst was added in one portion. The reaction was put under a hydrogen blanket and the reaction was stirred vigorously for 90 minutes when the reaction was judged essentially complete by GLC analysis. The reaction mixture was isolated by filtering-off the catalyst over a plug of methanol damp celite filter aid. The methanol was removed under reduced pressure to yield 0.85 equivalents of (1R,2S)-dihydroxy-1,2,3,4-tetrahydronaphthalene an off-white solid. $[\alpha]_D^{25}$=−28°, C=0.8, $CHCl_3$, melting point 119°–120° C.

iii) Preparation of (1R,2S)-1,2-dimesyloxy-1,2,3,4-tetrahydronaphthalene (X in which $R^1$ is $CH_3$).

One mole equivalent of cis-(1R,2S)-1,2-dihydroxy-1,2,3,4-tetrahydronaphthalene was dissolved in 30 volume equivalents of dichloromethane. Four mole equivalents of triethylamine were added and the solution cooled to −20° C. using a salt/ice bath. To the stirred solution 4 mole equivalents of methanesulfonyl chloride in 2 volume equivalents of dichloromethane were added dropwise. The solution was then allowed to warm to room temperature. The reaction mixture was washed twice with 0.5 volume equivalents of water and the reaction mixture was stirred for 15 minutes with 0.5 volume equivalents of saturated sodium carbonate solution. The organic layer was separated and the dichloromethane removed using vacuum rotary distillation to yield (1R,2S)-1,2-dimesyloxy-1,2,3,4-tetrahydronaphthalene as a crude oil ($^1$HNMR,H1=5.85, d, 1H; H2=5.05,m,1H; H3 and H4 complex; H5–8=7.1–7.5,m,4H; $SO_2CH_3$=3.00 and 3.08, s,3H and 3H).

iv) Preparation of (1S,2R)-1,2,-epoxy-1,2,3,4-tetrahydronaphthalene (I).

One mole equivalent of (1R,2S)-1,2-dimesyloxy-1,2,3,4-tetrahydronaphthalene was dissolved in 180 volume equivalents of toluene and 30 volume equivalents of 10% aqueous caustic potash was added together with 0.05 weight equivalents of tetrabutylammonium bromide. The mixture was stirred vigorously at ambient temperature for 4 hours when the reaction was judged essentially complete by GLC analysis. The organic layer was separated and washed three times with 0.25 volume equivalents of water. The solvent was removed by vacuum rotary distillation to give a crude brown oily product. The product was purified by column chromatography using Silica Gel 60 and a mixture of hexane and dichloromethane as eluent. The first fraction, after evaporation of the solvent, gave 0.26 mole equivalents of (1S,2R)-1,2-epoxy-1,2,3,4-tetrahydronaphthalene which had an optical rotation $[\alpha]_D^{22}$=−133° (C=0.21,$CHCl_3$). This compares with the literature value (see below) for (1R,2S)-1,2-epoxy-1,2,3,4-tetrahydronaphthalene of $[\alpha]_D$32 +133° (C=0.39,$CHCl_3$). Chiral GLC analysis showed the product to be >99.8% enantiomeric excess. Melting point 47°–48° C. J.Chem.Soc.Perkin.Trans I, 1979, 2437 quotes 45°–48° C. $^1$HNMR: H1=3.95,d,1H; H2=3.75,dt,1H; H3=1.65 and 2.3, m,2H; H4=2.55,m,2H; H5–H8=7.1–7.5,m,4H.

EXAMPLE 2

Preparation of (1R,2S)-1,2-epoxy-1,2,3,4-tetrahydronaphthalene (IA)

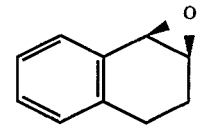

i) Preparation of cis-(1R,2S)-1,2-dihydroxy-1,2-dihydronaphthalene (II) as per Example 1i) above.

ii) Preparation of cis-(1R,2S)-1,2-dihydroxy-1,2,3,4-tetrahydronaphthalene (V) as per Example 1ii) above.

Alternatively (V) may be prepared as follows:

Palladium on charcoal catalyst (10%; 0.110 g) was added to a solution in ethanol (200 ml) of cis-(1R,2S)-1,2-dihydroxy-1,2-dihydronaphthalene (II) (1.9 g, 12 mmol) ($[\alpha]_D$+244° in chloroform), and the solution hydrogenated at atmospheric pressure. When hydrogenation was complete, the reaction mixture was filtered through a pad of filter aid and the filtrate evaporated under reduced pressure to yield a white solid (1.8 g, 95% yield), melting point 130°–131° C. after recrystallisation from a mixture of dichloromethane and hexane, and an optical rotation $[\alpha]_D$=−39° measured in chloroform solution. The mass spectrum and proton magnetic resonance spectrum were consistent with the identification of the compound as cis-(1R,2S)-1,2-dihydroxy-1,2,3,4-tetrahydronaphthalene.

iii) Preparation of 2'(S)-methoxy-2'-methyl-9b(R),3a(S)-methylenedioxy-9b,3a,4,5-tetrahydronaphthalene (VII in which R is $CH_3$ and $R^3$ is methyl) and 2'(R)-methoxy-2'-methyl-9b(R),3a(S)-methylenedioxy-9b,3a,4,5-tetrahydronaphthalene (VIIB in which R is $CH_3$ and $R^3$ is methyl).

To 1 mole equivalent of cis-(1R,2S)-1,2-dihydroxy-1,2,3,4-tetrahydronaphthalene in 25 equivalents of toluene at 60° C., 0.03 mole equivalents of benzoic acid were added. The mixture was stirred and 1 mole equivalent of trimethylorthoacetate was added slowly. The solution was stirred for 105 minutes under a blanket of nitrogen and then cooled to ambient temperature. One mole equivalent of sodium carbonate was added and the solution stirred for 30 minutes, before filtering and removing the solvents under reduced pressure to give 0.98 mole equivalents of a mixture of diastereomers in a 60:40 ratio. The diastereomers are separated by column chromatography using Keiselgel 60 Silica and a mixture of hexane and ethylacetate as eluent. $^1$HNMR (VII) H1=5.0,d,1H; H2=4.45,m,1H; H3=1.7,m; H4=2.2,m; H5–58=7.0,m,4H. Me=1.25,s,3H; OMe=3.1,s,3H.

(VIIB) H1=2.49,d,1H; H2=4.35,m,1H; H3=1.7,m; H4=2.2,m; H5–H6=7.0,m,4H; Me=1.35,s,3H; OMe=2.6,s, 3H.

iv) Preparation of trans-2(S)-acetoxy-1(S)-chloro-1,2,3,4-tetrahydronaphthalene (IX in which X is —Cl).

Compound (VII) and (VIIB) from 2iii) above (0.61 g, 2.7 mmol) was dissolved in dichloromethane (12 mmol) and treated with triethylamine (1 ml) and chlorotrimethylsilane (0.8 ml, 6.25 mmol) in dichloromethane (8 ml). The mixture was stirred under nitrogen at 0° C. for 2 hours. The solvent was removed under reduced pressure to give a brown oil (0.6 g, 96% yield). PLC purification (20% diethylether/petroleum ether b.p. 40°–60° C.) gave trans-2(S)-acetoxy-1(R)-chloro-1,2,3,4-tetrahydronaphthalene (IX in which X=Cl) as a white solid with a melting point of 44° C. after recrystallisation from a mixture of chloroform and petroleum ether (b.p. 40°–60° C.). The mass spectrum and proton magnetic resonance spectrum were consistent with the structure assigned. The value of $[\alpha]_D$ was −30° measured in chloroform.

v) Preparation of (1R,2S)-1,2-epoxy-1,2,3,4-tetrahydronaphthalene (IA).

To a solution of 1 mole equivalent trans-2(S)-acetoxy-1(R)-chloro-1,2,3,4-tetrahydronaphthalene in 100 volume equivalents of tetrahydrofuran at 0° C., 12 mole equivalents of sodium methoxide were added. The solution was stirred at 0° C. for $2^H$ and then allowed to stand overnight at 4° C. The solution was filtered and the solvent removed by vacuum rotary distillation to give an orange oil. The produce was crystallised from the oil by dissolving in a minimum of a mixture diethylether and pentane. Yield of isolated product 0.58 mole equivalents. Melting point 45°–47° C. (M. N. Akhtar, D. R. Boyd, J. G. Hamilton, J.Chem. Soc. Perkin. Trans I, 1979, 2437 quotes m.p. 45°–48° C.). $[\alpha]_D$=+133° (C=0.39,CHCl$_3$).

EXAMPLE 3

Preparation of cis-(1R,2S)-1,2-dihydroxy-syn-3,4-epoxy-1,2,3,4-tetrahydronaphthalene (III)

Phosphate buffer solution (pH 8, 50 ml) was added to a solution of cis-(1R,2S)-1,2-dihydroxy-1,2-dihydronaphthalene (II) (1.6 g, 6.1 mmol) in dichloromethane (50 ml). m-Chloroperoxybenzoic acid (2.12 g, 12 mmol) was then added in two equal portions, the first while stirring at 0° C., the second after 2 hours. The mixture was then stirred vigorously overnight at room temperature. The organic layer was then separated and washed with 10% sodium sulphite solution (20 ml), followed by 10% sodium bicarbonate solution (20 ml), dried over magnesium sulphate and evaporated. The residue, a clear oil (0.63 g, 63% yield) crystallised from a mixture of dichloromethane and hexane. The product was identified by its mass spectrum and proton magnetic resonance spectrum as cis-(1R,2S)-1,2-dihydroxy-syn-3,4-epoxy-1,2,3,4-tetrahydronaphthalene (III) having a melting point of 78°–79° C. and $[\alpha]_D$–52° (measured in chloroform). The phosphate buffer solution used above was prepared by adding a solution of sodium dihydrogen orthophosphate (0.1M, about 20 ml) to a solution of disodium hydrogen orthophosphate (0.1M, 500 ml) until a pH of 8 was reached.

EXAMPLE 4

Preparation of (1S,2R)-1,2-dihydroxy-1,2-dihydronaphthalene a) Innoculum Preparation The innoculum was prepared by picking off several active colonies of Pseudomonas putida NC1B 11767 growing on agar plates with 0.11% pyruvate. The colonies were transferred using sterile techniques to 10 ml of 0.85% saline solution in a 25 ml sterile jar. The cells were uniformly dispersed in the solution by vortexing for several minutes. The solution was transferred, again using sterile techniques to a 1 liter baffled side arm inoculum flask and plugged with foam bung. The flask contained 200 ml of solution made up of 0.96 g KH$_2$PO$_4$, 1.23 g K$_2$HPO$_4$, 3.00 g NH$_4$Cl, 0.40 g MgSO$_4$.7H$_2$O and 1.9 ml of trace elements per liter. The solution was made up to pH 7.0 using 2M KOH or 1MH$_2$SO$_4$ prior to sterilisation.

The trace elements solution comprised 50 g Na$_2$EDTA, 2.20 g ZnSO$_4$.7H$_2$O, 5.54 g CaCl$_2$, 5.06 g MnCl$_2$.4H$_2$O, 5.00 g FeSO$_4$.7H$_2$O, 1.10 g (NH$_4$)$_6$Mo$_7$O$_{24}$.4H$_2$O, 1.57 g CuSO$_4$.5H$_2$O and 1.61 g CoCl$_2$.6H$_2$O per liter of distilled water. Initially the Na$_2$EDTA was dissolved alone by adjusting the solution to a pH value of 6.0 with potassium hydroxide (2M). The other components were then dissolved sequentially in the order shown above. Finally the pH value was again adjusted to 6.0 with the potassium hydroxide solution.

All cultures were grown at 30° C. on an orbital shaker at 200 rpm.

Pseudomonas putida 11767, which did not express an active ring hydroxylating dioxygenase enzyme was grown on 0.48% sodium pyruvate together with 0.1% toluene as an inducer for dioxygenose activity.

b) Fermentation

Pseudomonas putida 11767 was grown in a 10 liter fermenter. The organisms were grown at 30° C., at a pH value of 7.0, an air supply flow rate of 51 min$^{-1}$, a media volume of 9 liters and a stirrer speed of 500 rpm. Under these conditions growth was oxygen limited. The same basic medium used for the growth of non-recombinant organisms in shake-flasks was used in 10 liter fermentations. The microorganism was grown with toluene as the sole source of carbon and energy. The air supply to the fermenter was passed through a reservoir of toluene (500 ml), so that toluene-saturated air was continuously fed to the formenter during growth.

An inoculum of 200 ml was used, prepared as previously described.

c) Biotransformation

Cultures of Pseudomonas putida 11767 were grown in 10 liters of medium. Racemic-1,2-dihydro-1,2-dihydroxynaphthalene was added directly to cultures that had reached the late exponential phase of growth. Cultures grown on toluene were initially purged of any remaining arene with toluene-free air for 10 minutes, prior to addition of the racemic-1,2-dihydro-1,2-dihydroxynaphthalene. It was assumed that most of the remaining toluene was removed from the reactor during this period.

The biotransformation was a batch reaction with the racemic-1,2-dihydro-1,2-dihydroxynaphthalene added at the start of the reaction to a concentration of 1 mg.ml$^{-1}$ (for solids). Glucose was used as a co-substrate in this biotransformation, at a concentration of 4.8 g l$^{-1}$. The pH was adjusted to pH 7.2 for biotransformation purposes, but other reactor conditions were the same as those used during growth of the biocatalyst.

d) Isolation of Product

Isolation of 1,2-dihydro-(1S,2R)-dihydroxynaphthalene was carried out as for 1,2-dihydro-(1R,2S)-dihydroxynaphthalene described in Example 1i)d).

The structure of 1,2-dihydro-(1S,2R)-dihydroxynaphthalene was confirmed by $^1$HNMR, optical rotation $[\alpha]_D^{25}$=−243° (C=0.175 CHCl$_3$) and its comigration on HPLC with the enantiomer.

We claim:

1. A process for the preparation of (1S,2R)-1,2-epoxy-1,2,3,4-tetrahydronaphthalene having the Formula (I):

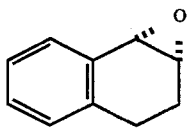

Formula (I)

which comprises the steps of (a) hydrogenating the compound of Formula (II) to form cis-(1R, 2S)-1,2-dihydroxy-1,2,3,4-tetrahydronaphthalene having the Formula (V):

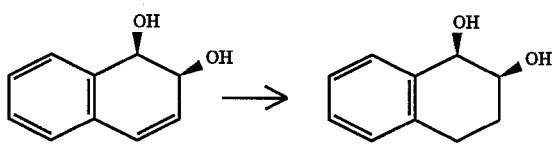

Formula (II)  Formula (V)

(b) reacting the dihydroxy compound of Formula (V) with a sulphonyl halide of formula $R^1SO_2Z$ wherein $R^1$ is methyl, ethyl, trifluoromethyl, phenyl or p-tolyl, and Z is fluorine, chlorine, bromine or iodine to give a bis-sulphonyl ester of formula (X):

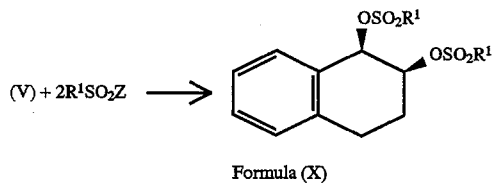

Formula (X)

and (c) treating the bis-sulphonyl ester (X) with an alkali metal carbonate or alkali metal hydroxide to give the compound of Formula (I).

2. A process for the preparation of (1R,2S)-1,2-epoxy-1,2,3,4-tetrahydronaphthalene having the Formula (IA):

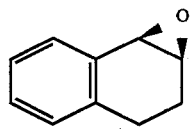

Formula (IA)

which comprises the steps of a) hydrogenating the compound of Formula (II) to form cis-(1R,2S)-1,2-dihydroxy-1,2,3,4-tetrahydronaphthalene of Formula (V):

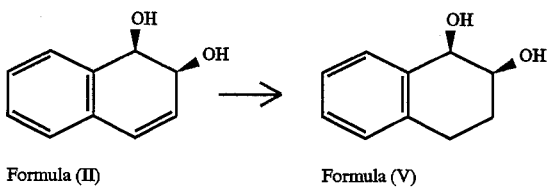

Formula (II)  Formula (V)

b) reacting the compound of Formula (V) with an alkyl orthoalkanoate of Formula (VI) to form a mixture of dioxolane diastereoisomers of Formula (VII) and (VIIB):

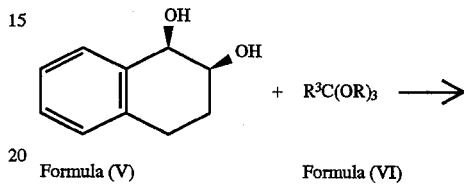

Formula (V)  Formula (VI)

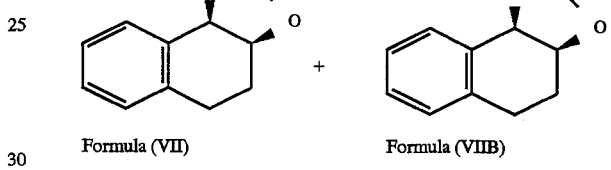

Formula (VII)  Formula (VIIB)

in which R is alkyl and $R^3$ is H, alkyl or phenyl;

c) reacting the mixture of dioxolane diastereoisomers of Formulae (VII) and (VIIB) with a halotrialkyl- or halotriarylsilane of Formula (XIV) to form a compound of Formula (IX):

(VII) + (VIIB) + $(R^2)_3SiX$ 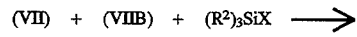

Formula (XIV)

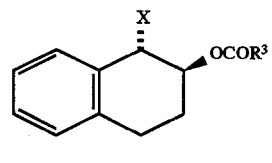

Formula (IX)

in which:
$R^2$ is alkyl or aryl;
X is —Cl, —Br or —I; and
$R^3$ is as hereinbefore defined;

d) reacting the compound of Formula (IX) with an alkali metal alkoxide to form (1R,2S)-1,2-epoxy-1,2,3,4-tetrahydronaphthalene having the Formula (IA).

* * * * *